US008824754B2

(12) United States Patent
Halmann

(10) Patent No.: US 8,824,754 B2
(45) Date of Patent: *Sep. 2, 2014

(54) METHOD AND APPARATUS FOR GENERATING VARIABLE RESOLUTION MEDICAL IMAGES

(75) Inventor: Nahi Halmann, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 8 days.

This patent is subject to a terminal disclaimer.

(21) Appl. No.: 13/294,786

(22) Filed: Nov. 11, 2011

(65) Prior Publication Data

US 2012/0057767 A1    Mar. 8, 2012

Related U.S. Application Data

(63) Continuation of application No. 11/710,696, filed on Feb. 23, 2007, now Pat. No. 8,073,211.

(51) Int. Cl.
| | | |
|---|---|---|
| *G06K 9/00* | (2006.01) | |
| *G03B 42/06* | (2006.01) | |
| *A61B 8/00* | (2006.01) | |
| *G06T 3/40* | (2006.01) | |

(52) U.S. Cl.
CPC . *G03B 42/06* (2013.01); *A61B 8/00* (2013.01); *A61B 8/4472* (2013.01); *A61B 8/461* (2013.01); *G06T 3/4092* (2013.01)
USPC ............ 382/128; 382/299; 382/300; 382/313

(58) Field of Classification Search
None
See application file for complete search history.

(56) References Cited

U.S. PATENT DOCUMENTS

| | | | | |
|---|---|---|---|---|
| 5,161,535 | A |  | 11/1992 | Short et al. |
| 5,172,103 | A | * | 12/1992 | Kita ............................... 345/667 |
| 5,471,989 | A |  | 12/1995 | Roundhill et al. |
| 5,612,715 | A | * | 3/1997 | Karaki et al. .................. 345/698 |
| 5,856,821 | A | * | 1/1999 | Funahashi ...................... 345/667 |
| 6,106,472 | A |  | 8/2000 | Chiang et al. |
| 6,228,030 | B1 | * | 5/2001 | Urbano et al. ................ 600/443 |
| 6,251,073 | B1 |  | 6/2001 | Imran et al. |
| 6,278,975 | B1 |  | 8/2001 | Brant et al. |
| 6,440,072 | B1 | * | 8/2002 | Schuman et al. .............. 600/437 |
| 6,442,289 | B1 | * | 8/2002 | Olsson et al. .................. 382/128 |
| 6,480,619 | B1 | * | 11/2002 | Vuylsteke et al. ............. 382/132 |
| 6,520,912 | B1 | * | 2/2003 | Brooks et al. ................. 600/437 |

(Continued)

FOREIGN PATENT DOCUMENTS

| | | |
|---|---|---|
| EP | 0 520 338 A2 | 12/1992 |
| EP | 1211982 A1 | 6/2002 |

(Continued)

*Primary Examiner* — Jayesh A Patel
(74) *Attorney, Agent, or Firm* — Dean D. Small; The Small Patent Law Group

(57) ABSTRACT

A hand carried medical imaging device includes a probe configured to acquire raw medical image data, an integrated display, a data memory configured to store the acquired raw medical image data, a back end processor, and a user interface operably coupled to the back end processor configured to receive commands from a user and to instruct the back end processor to display the produced medical image on the integrated display at a first resolution, and to either produce and send either the medical image at the second, higher resolution, to send the acquired raw image data, or both, to the external device, in accordance with the commands from the user.

31 Claims, 5 Drawing Sheets

(56) References Cited

U.S. PATENT DOCUMENTS

| | | | |
|---|---|---|---|
| 6,540,682 B1 | 4/2003 | Leavitt et al. | |
| 6,549,214 B1 * | 4/2003 | Patel et al. | 345/660 |
| 6,556,724 B1 * | 4/2003 | Chang et al. | 382/299 |
| 6,569,097 B1 | 5/2003 | McMorrow et al. | |
| 6,630,937 B2 * | 10/2003 | Kallergi et al. | 345/619 |
| 6,630,938 B1 * | 10/2003 | Nanni | 345/629 |
| 6,692,442 B2 * | 2/2004 | Brock-Fisher et al. | 600/458 |
| 6,980,419 B2 | 12/2005 | Smith et al. | |
| 7,052,460 B2 * | 5/2006 | Liu et al. | 600/443 |
| 7,148,909 B2 * | 12/2006 | Yui et al. | 345/660 |
| 7,312,764 B2 * | 12/2007 | Driver et al. | 345/1.1 |
| 7,835,596 B2 * | 11/2010 | Hornback et al. | 382/303 |
| 8,022,979 B2 * | 9/2011 | Miyamoto et al. | 348/65 |
| 8,144,191 B2 * | 3/2012 | Kawanishi et al. | 348/65 |
| 8,533,366 B2 * | 9/2013 | Ichieda | 710/5 |
| 2001/0041991 A1 | 11/2001 | Segal et al. | |
| 2003/0065260 A1 * | 4/2003 | Cheng et al. | 600/427 |
| 2003/0073894 A1 | 4/2003 | Chiang et al. | |
| 2003/0090592 A1 * | 5/2003 | Callway et al. | 348/581 |
| 2003/0220573 A1 * | 11/2003 | Imran et al. | 600/459 |
| 2003/0222895 A1 * | 12/2003 | Arai | 345/698 |
| 2004/0133526 A1 * | 7/2004 | Shmueli et al. | 705/80 |
| 2005/0010098 A1 * | 1/2005 | Frigstad et al. | 600/407 |
| 2005/0054913 A1 * | 3/2005 | Duerk et al. | 600/423 |
| 2005/0059892 A1 * | 3/2005 | Dubois et al. | 600/443 |
| 2005/0154303 A1 * | 7/2005 | Walker et al. | 600/443 |
| 2005/0228281 A1 * | 10/2005 | Nefos | 600/446 |
| 2005/0288584 A1 | 12/2005 | McMorrow et al. | |
| 2006/0025684 A1 | 2/2006 | Quistgaard et al. | |
| 2006/0039105 A1 * | 2/2006 | Smith et al. | 361/681 |
| 2006/0045318 A1 * | 3/2006 | Schoisswohl et al. | 382/128 |
| 2006/0074310 A1 * | 4/2006 | Thiele | 600/437 |
| 2006/0203087 A1 * | 9/2006 | Kawanishi et al. | 348/65 |
| 2006/0233516 A1 * | 10/2006 | Kimura | 386/68 |
| 2006/0239540 A1 * | 10/2006 | Serra et al. | 382/154 |
| 2006/0240862 A1 * | 10/2006 | Neven et al. | 455/550.1 |
| 2007/0002050 A1 * | 1/2007 | Aoki et al. | 345/428 |
| 2007/0016029 A1 * | 1/2007 | Donaldson et al. | 600/437 |
| 2007/0019887 A1 * | 1/2007 | Nestares et al. | 382/299 |
| 2007/0036402 A1 * | 2/2007 | Cahill et al. | 382/128 |
| 2007/0049824 A1 * | 3/2007 | Konofagou et al. | 600/437 |
| 2007/0188604 A1 * | 8/2007 | Miyamoto et al. | 348/65 |
| 2007/0237295 A1 * | 10/2007 | Gundel | 378/62 |
| 2008/0011628 A1 * | 1/2008 | Lin | 206/307 |
| 2009/0058884 A1 * | 3/2009 | Li et al. | 345/660 |
| 2009/0265290 A1 * | 10/2009 | Ciaramita et al. | 706/12 |

FOREIGN PATENT DOCUMENTS

| | | |
|---|---|---|
| JP | 04090749 A2 | 3/1992 |
| JP | 05220142 A2 | 8/1993 |
| JP | 2002085405 A | 3/2002 |
| JP | 2002177266 A | 6/2002 |
| JP | 2003507114 A | 2/2003 |
| JP | 2006519684 A | 8/2006 |
| WO | WO 01/13796 A1 | 3/2001 |
| WO | WO 2004/080364 A2 | 9/2004 |

* cited by examiner

METHOD AND APPARATUS FOR GENERATING VARIABLE RESOLUTION MEDICAL IMAGES

CROSS REFERENCE TO RELATED APPLICATIONS

This application is a continuation of and claims priority and the benefit of the filing date of U.S. application Ser. No. 11/710,696, filed Feb. 23, 2007 and entitled "METHOD AND APPARATUS FOR VARIABLE RESOLUTION MEDICAL IMAGES", the subject matter of which is hereby incorporated by reference in its entirety.

BACKGROUND OF THE INVENTION

This invention relates generally to handheld and hand-carried ultrasound (or other medical imaging) systems having integrated displays.

Handheld and hand-carried ultrasound systems often include an integrated display (usually an LCD) that allows the user to view the images while scanning as well as retrieve images from internal storage device. Often, these systems are used in conjunction with external medical devices such as a PACS (Picture Archiving and Communication System) system, a workstation, and/or an external printer. Often, these external systems can support display resolutions higher than that achievable with the internal display of the hand-carried ultrasound system. However, images from the handheld or hand-carried ultrasound systems do not provide image data at a resolution sufficient to support the higher display resolutions of the external systems.

BRIEF DESCRIPTION OF THE INVENTION

In an exemplary embodiment, a hand carried medical imaging device is provided that includes a probe configured to acquire raw medical image data, an integrated display, a data memory configured to store the acquired raw medical image data, a back end processor, and a user interface operably coupled to the back end processor configured to receive commands from a user and to instruct the back end processor to display the produced medical image on the integrated display at a first resolution. The user interface is also configured to either produce and send either the medical image at a second, higher resolution, to send the acquired raw image data, or both, to the external device, in accordance with the commands from the user.

In another exemplary embodiment, a method for operating a hand carried medical imaging device is provided. The device includes a probe configured to acquire raw medical image data, an integrated display configured to display a medical image, a data memory configured to store the acquired raw medical image data, a back end processor and a user interface. The user interface is operably coupled to the back end processor and is configured to receive commands from a user and to instruct the back end processor to display a produced medical image on the integrated display at a first resolution. The user interface is also configured to either produce and send either the medical image at a second, higher resolution, to send the acquired raw image data, or both, to an external device, in accordance with the commands from the user. The method includes storing raw medical image data in a coordinate system of the probe, and, in accordance with instructions received via the user interface, either performing a scan conversion on the raw medical image data and displaying a resulting medical image at a first resolution on the integrated display; or at least one of transferring raw data to the external device for further processing or storage, or performing a scan conversion on the raw medical image data and displaying a resulting medical image at a second, higher resolution on an external display.

In yet another exemplary embodiment, a machine readable medium or media is provided having recorded thereon instructions configured to instruct a processor in a hand carried medical imaging device to acquire and store raw medical image data in a coordinate system of a probe on a data memory, and, in accordance with instructions received via a user interface, either perform a scan conversion on the raw medical image data and display a resulting medical image at a first resolution on an integrated display; or at least one of transfer raw data to an external device for further processing or storage, or perform a scan conversion on the raw medical image data and display a resulting medical image at a second, higher resolution on an external display.

Figure 1:
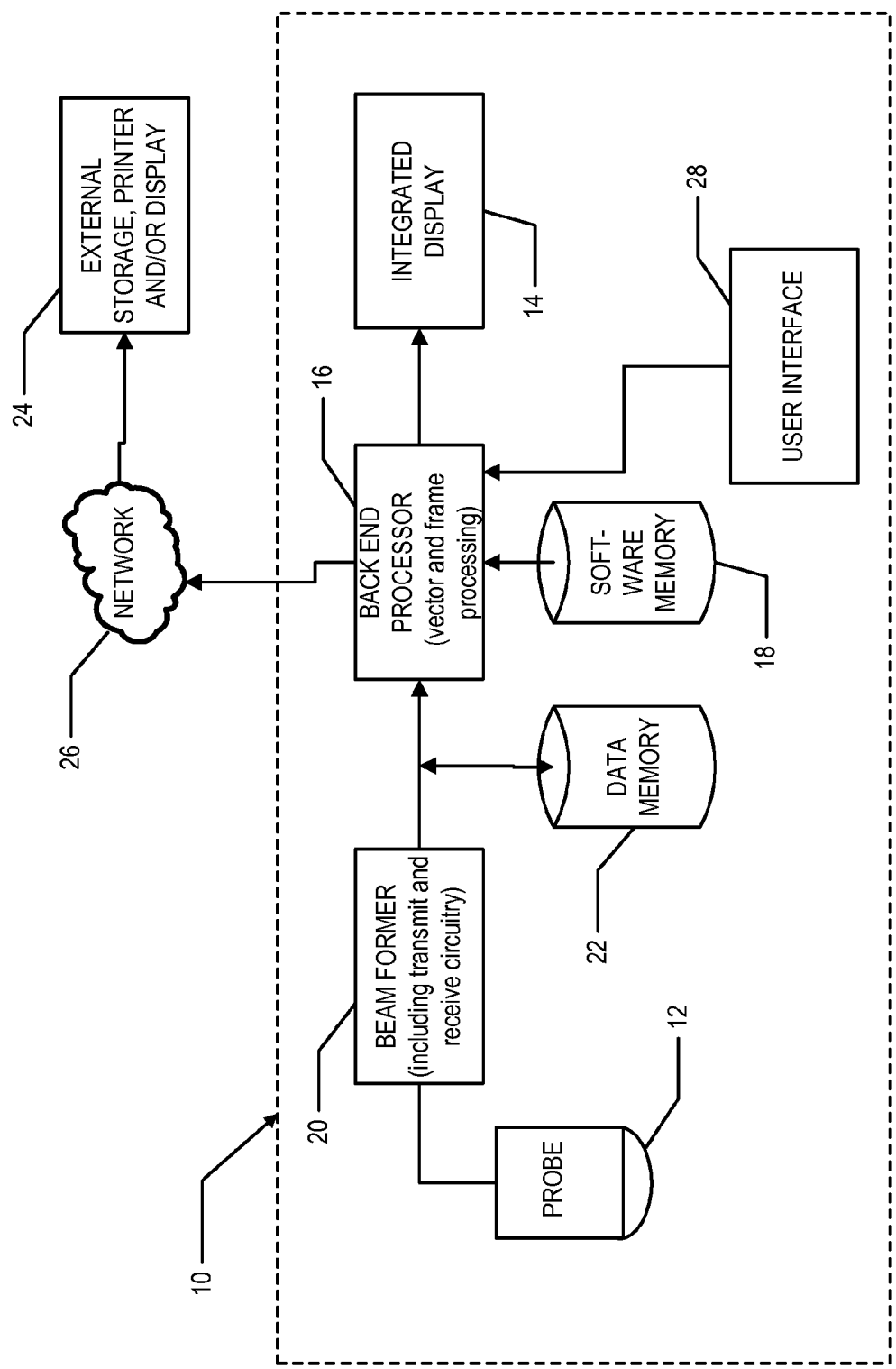
FIG. 1 is a block diagram of a hand carried or hand-held medical imaging device having a probe or transducer configured to acquire raw medical image data formed in accordance with various embodiments of the invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

DETAILED DESCRIPTION OF THE INVENTION

As used herein, an element or step recited in the singular and proceeded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Technical results of the present invention include the transmission of high resolution medical images and/or high resolution raw medical image data across a wired or wireless network, or across a dedicated connection. The present description details how these results are achieved in some embodiments of the present invention.

FIG. 1 is a block diagram of a handheld or hand carried medical imaging device 10 having a probe or transducer 12 configured to acquire raw medical image data. In some embodiments, probe 12 is an ultrasound transducer and hand carried medical imaging device 10 is an ultrasound imaging apparatus. An integrated display 14 (e.g., an internal display) is also provided and is configured to display a medical image. A data memory 22 stores acquired raw image data, which may be processed by a beam former 20 in some embodiments of the present invention.

To display a medical image using probe 12, a back end processor 16 is provided with a software or firmware memory 18 containing instructions to perform frame processing, scan conversion, and resolution selection using acquired raw medical image data from probe 12, possibly further processed by beam former 20 in some configurations. Dedicated hardware may be used instead of software for performing scan conversion, or a combination of dedicated hardware and software, or software in combination with a general purpose processor or a digital signal processor. Once the requirements for such software and/or hardware and/or dedicated hardware are gained from an understanding of the descriptions of embodiments of the invention contained herein, the choice of any particular implementation may be left to a hardware engineer and/or software engineer. However, for purposes of the present disclosure, any dedicated and/or special purpose hardware or special purpose processor is considered subsumed in the block labeled "back end processor 16."

Software or firmware memory 18 can comprise a read only memory (ROM), random access memory (RAM), a miniature hard drive, a flash memory card, or any kind of device (or devices) configured to read instructions from a machine-readable medium or media. The instructions contained in software or firmware memory 18 further include instructions to produce a medical image of suitable resolution for display on integrated display 14, and to send acquired raw image data stored in a data memory 22 to an external device 24 in a higher resolution, for example, a resolution higher than the highest resolution that can be displayed on integrated display 14. The image data of higher resolution and/or the raw medical image data itself may be sent from back end processor 16 to external device 24 via a wired or wireless network (or direct connection, for example, via a serial or parallel cable or USB port) 26 under control of processor 16 and user interface 28. In some embodiments, external device 24 may be a computer or a workstation having a display. In some other embodiments, external device 24 may be a separate external display or a printer capable of receiving image data from hand carried medical imaging device 10 and of displaying or printing images having greater resolution than integrated display 14.

A user interface 28 (that may also include integrated display 14) is provided to receive commands from a user and to instruct back end processor 16 to display the acquired raw image data on integrated display 14, send the acquired raw image data to external device 24 in a higher resolution than that displayable on integrated display 14, or both, in accordance with the commands from the user.

Figure 2:
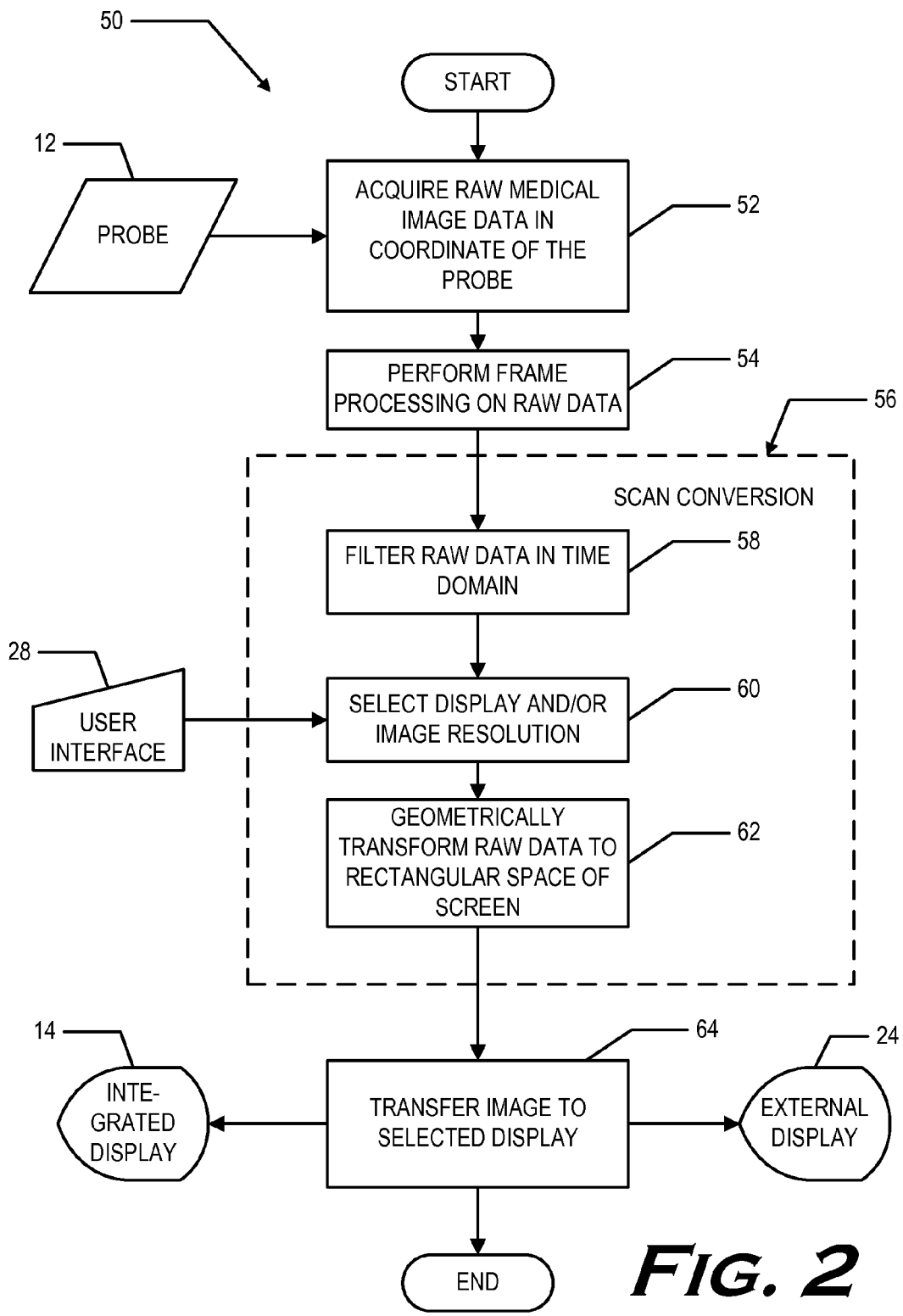
FIG. 2 is a flow chart of a method that can be performed by the hand carried medical imaging device of FIG. 1.

FIG. 2 is a flow chart 50 of a method that can be performed by the hand carried medical imaging device 10 of FIG. 1. Referring to FIG. 2, at 52, hand carried medical imaging device 10 is operated to acquire raw medical image data in the coordinates of medical transducer or probe 12. This step of the method may involve the cooperation of beam former 20, data memory 22 (where the raw medical image data is stored), and back end processor 16, under the instruction of software stored in software memory 18. At 54, frame processing is performed on raw medical image data by back end processor 16 under instruction of software stored in software memory 18. In some embodiments of the present invention, this step of the method includes accessing stored raw medical image data from data memory 22.

At 56, a scan conversion process is carried out that produces geometrically transformed data with a resolution appropriate for the size of display on which the medical image data is to be displayed as an image. More particularly, raw data is filtered in the time domain at 58. The temporal filtering at 58 can include, for example, frame averaging, so that each image frame that is displayed comprises data from more than one data frame. Temporal filtering also allows the separation of the display frame rate from the input raw data rate. More particularly, the rate at which a piezoelectric front end (e.g., a piezoelectric element 12 in an ultrasound imaging apparatus 10) scans and/or obtains data for image frames can be faster or slower than the display rate of the frames themselves. Next, at 60, a user selects a display and/or image resolution using user interface 28. For example, if integrated display 14 in hand carried medical imaging device 10 has a maximum resolution of 320×320 pixels, the user can select that the image be displayed on this device in up to 320×320 resolution.

If an external display 24 is selected (or an external storage device or printer), the user can specify the resolution of the image to be displayed on external display device 24 (or saved to the external storage device or printed on the printer). Next, at 62, the filtered data from 58 is geometrically transformed to the rectangular space of the display, in accordance with the selected display and/or image resolution from 60. For example, each line of echo raw data may comprise 1000 samples, wherein probe 12 "illuminates" and gathers data from a fan-like region of 100 lines, each with 1000 samples. The conversion at 62 transforms the data from a polar to a Cartesian coordinate system (for example) using averaging over a number of pixels (e.g., bilinear or trilinear) to reduce interpolation. In the case of bilinear averaging, each point on the result of the interpolation is the result of interpolating four neighboring data points. The neighboring points are, for example, four points from two rotated vectors that are averaged, each point being weighted appropriately. Finally, at 64, the geometrically transformed data from 62 is transferred either to integrated display 14 or external display 24, in accordance with the selection made at 60.

As a result, in some embodiments of the present invention, medical images can be displayed in a relatively low resolution (up to the highest resolution available) on relatively small integrated display 14, or displayed (or stored or printed) on an external device 24, possibly at a much higher resolution.

Flow chart 50 of FIG. 2 contemplates an embodiment in which scan conversion 56 for external devices 24 is performed by hand carried medical imaging device 10. However, in some embodiments, scan conversion 56 is not performed by hand carried medical imaging device 10 for external devices 24. Instead, raw medical image data from data memory 22 (optionally processed by beam former 20) is transferred directly from hand carried medical imaging device 10 to external storage, printer, and/or display 24 for further processing, as necessary. Flow chart 68 of FIG. 3 shows an example of one such embodiment.

Figure 3:
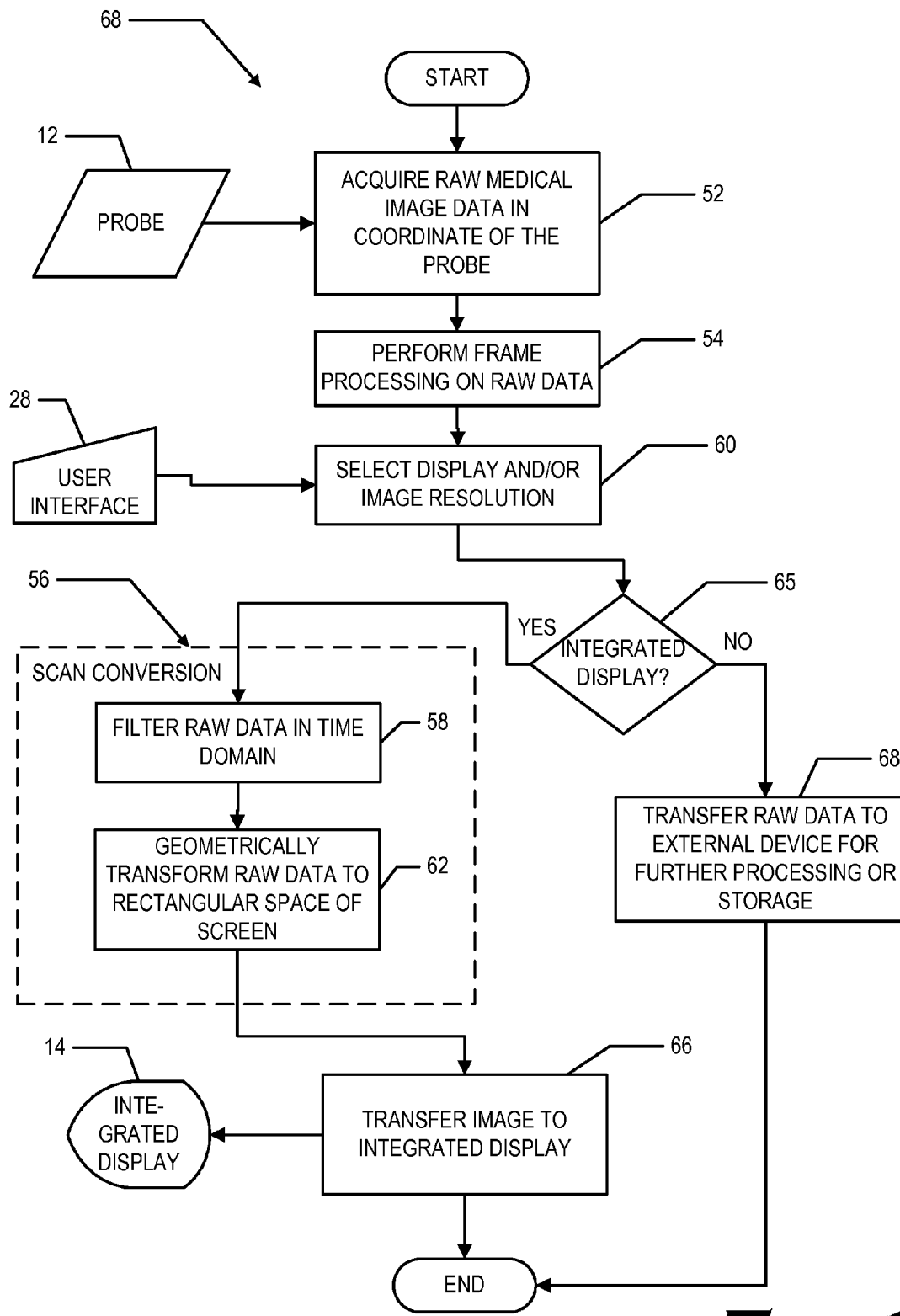
FIG. 3 is a flow chart of another method that can be performed by the hand carried medical imaging device of FIG. 1.

Referring to FIG. 3, at 52, hand carried medical imaging device 10 is operated to acquire raw medical image data in the coordinates of medical transducer or probe 12. This step of the method may involve the cooperation of beam former 20, data memory 22 (where the raw medical image data is stored), and back end processor 16, under the instruction of software stored in software memory 18. At 54, frame processing is performed on raw medical image data by back end processor 16 under instruction of software stored in software memory 18. In some embodiments of the present invention, this step of the method includes accessing stored raw medical image data from data memory 22, and may include either or both reading or storing the raw medical image data. (Thus, whenever "raw medical image data" is referred to herein, it may refer either to raw medical image data, with or without frame processing.) Next, at 60, information is obtained from the user of hand carried medical imaging device 10 concerning whether to display a medical image on integrated display 14, or to send it to an external device 24 for display, storage, and/or further processing.

If the user selected that the data be displayed on integrated display 14, then a decision is made at 65 to subject the raw medical image data to scan conversion at 56. In this case, the raw medical image data is filtered in the time domain at 58 and then geometrically transformed (at the appropriate resolution for integrated display 14 or at a lesser resolution chosen by the user) to the rectangular space of display 14. The image is then transferred to integrated display 14 at 66.

On the other hand, if the user selected that data be sent to external device 24, the raw medical image data itself is sent (in at least one embodiment, without further image processing or scan conversion) to external device 24 for further processing, storage, and/or display.

It should be understood that the functionalities of flow chart 50 and flow chart 68 may be combined in various ways, and that these flow charts are not intended to limit the functionality of various embodiments of the present invention. For example, in some embodiments of the present invention, both high resolution images (as in flow chart 50) and raw medical image data (as in flow chart 68) can be exported to an external device 24, or either, depending upon a selection made by the user and entered into user interface 28. Also, like steps in flow charts 50 and 68 represent similar processes.

Figure 4:
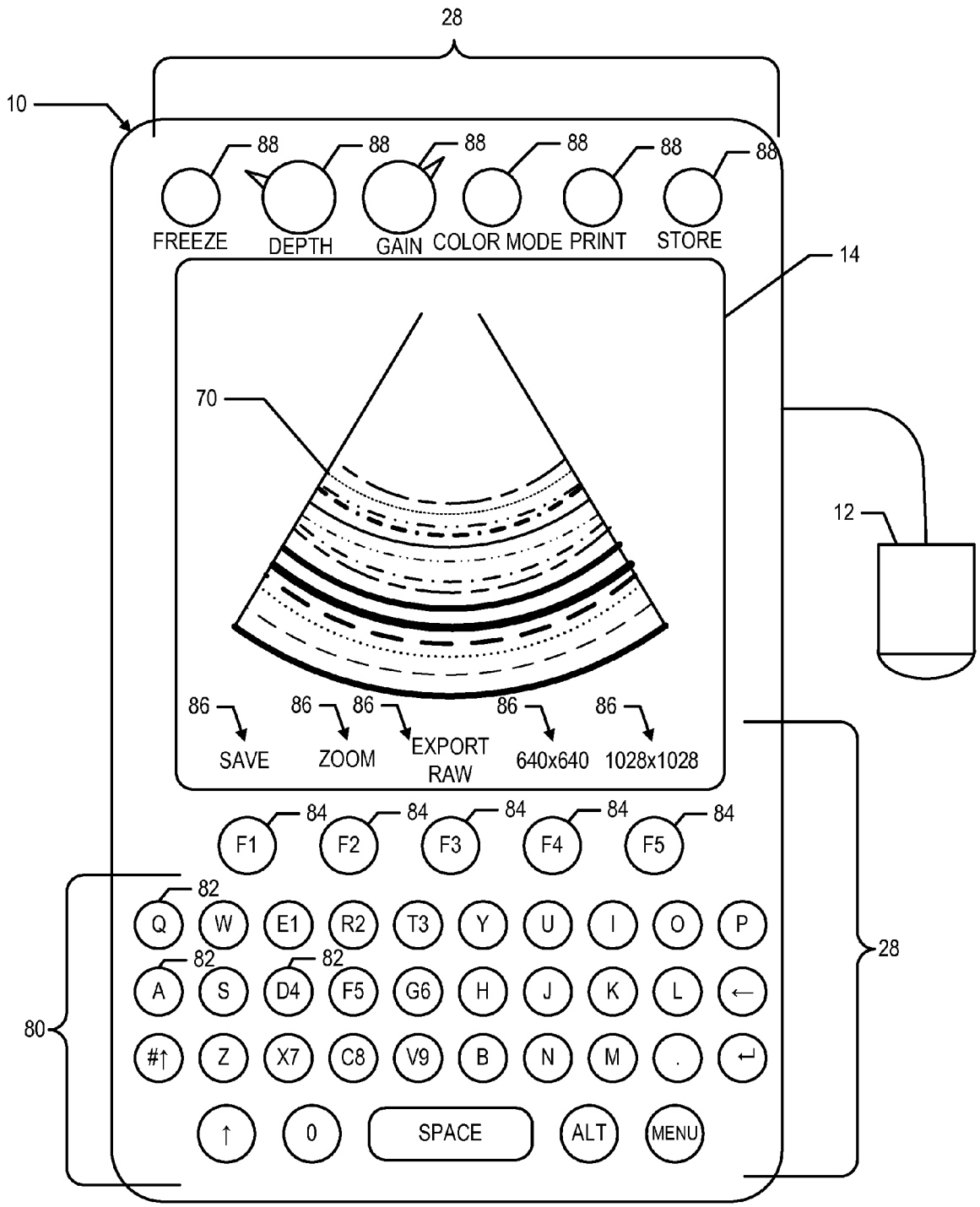
FIG. 4 is a pictorial drawing of a hand carried medical imaging device formed in accordance with an embodiment of the present invention.

FIG. 4 is a pictorial drawing of an embodiment of hand carried medical imaging device 10 of the present invention. Hand carried medical imaging device 10 includes the display 14, for example, a 320×320 pixel color LCD display (on which a medical image 70 may be displayed) and the user interface 28. In some embodiments of the present invention, a typewriter-like keyboard 80 of buttons 82 is included in user interface 28, as well as one or more soft keys 84 that may be assigned functions in accordance with the mode of operation of hand carried medical imaging device 10. A portion of display 14 may be devoted to labels 86 for soft keys 84. For example, the labels shown in FIG. 4 allow a user to save the current raw medical image data, to zoom in on a section of image 70 on display 14, to export raw medical image data to an external device 24, or to display (or export) an image having a resolution of either 640×640 pixels or 1028×1028 pixels on an external device 24 that includes a display. The device may also have additional keys and/or controls 88 for special purpose functions, which may include, but are not limited to "freeze," "depth control," "gain control," "color-mode," "print," and "store."

Figure 5:
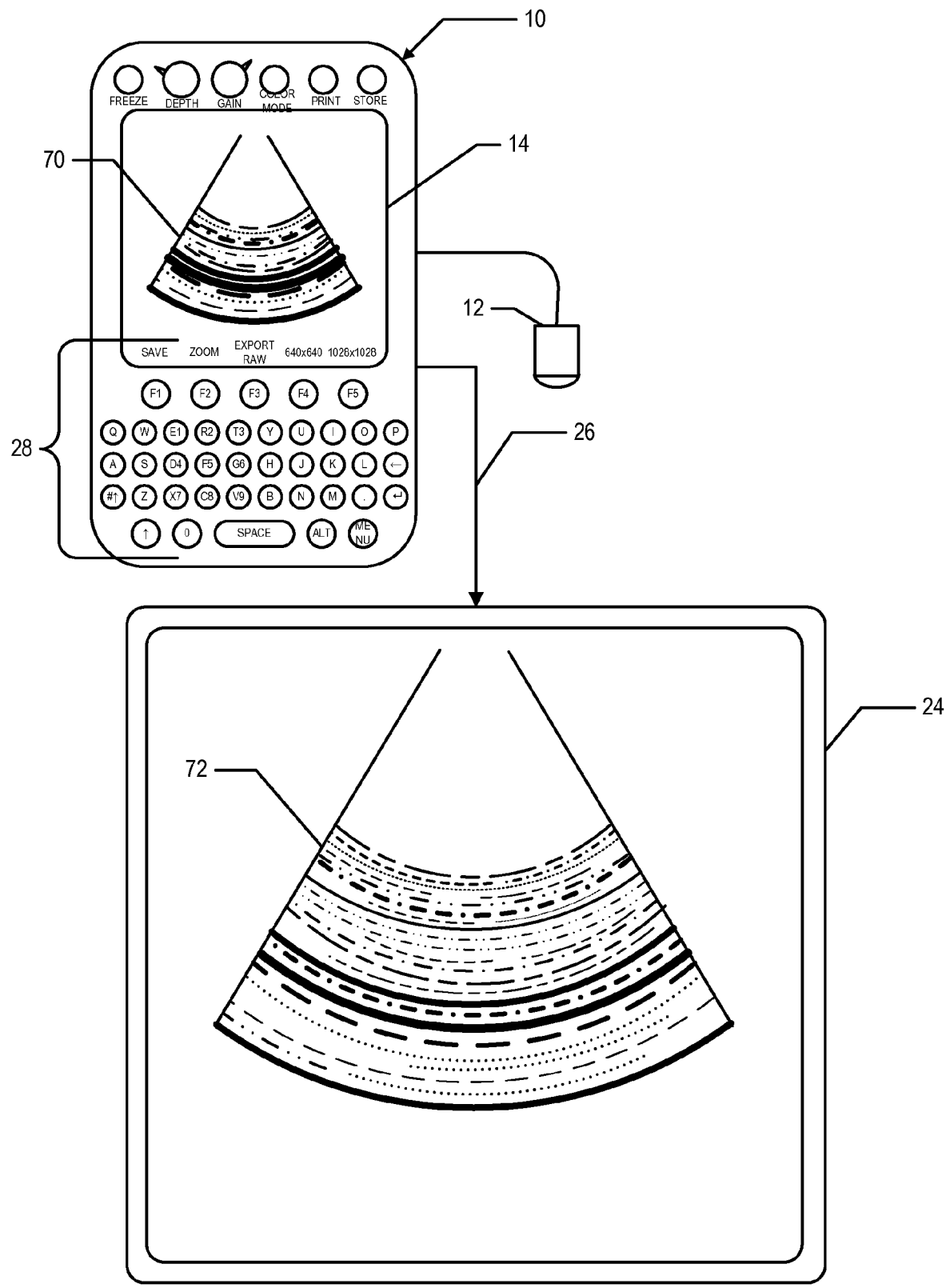
FIG. 5 is a pictorial drawing illustrating a hand carried medical imaging device directly connected to an external device in accordance with various embodiments of the invention.

FIG. 5 is a pictorial schematic drawing of hand carried medical imaging device 10 directly connected to an external device 24. Because hand carried medical imaging device 10 is capable of storing raw medical image data for export to external device 24 and/or processing data at a higher resolution than is available with integrated display 14, external device 24 can display a higher resolution version 72 of image 70. For example, external device 24 can have a display 24 that displays 1024×1024 pixels, whereas integrated display 14 may be capable of displaying only 320×320 pixels on account of its small size.

Thus, some embodiments of the present invention include the capability of visualizing image data in real time on integrated display 14 (albeit at relatively low resolution) while hand carried medical imaging device 10 is used on a patient, with raw medical image data stored in memory 22. Then, if needed, the raw medical image data can be transferred to an external memory, printer, or display 24 where another scan conversion can be performed. Neither the transfer nor the other scan conversion need be performed at the same time as image data is visualized on integrated display 14, nor need either be done at the same site where the image data is acquired. In cases in which scan conversion is done by hand carried medical imaging device 10 for an external device 24, images once displayed at relatively low resolution on integrated display 14 can be selected, and then regenerated and displayed at higher resolution on external device 24. In these cases, less time is required than is required to transfer the raw medical imaging data to external device 24. Also, there is no universal standard for transferring raw medical imaging data, but the high resolution images can be generated in JPEG or DICOM format and sent to an external display device 24. If only selected images are being sent in this manner, transmission between hand carried medical imaging device 10 and external device 24 can be made very efficient.

Other embodiments of the present invention provide a machine readable medium or media 18 having recorded thereon instructions configured to instruct a processor 16 in a hand carried medical imaging device 10 to acquire and store raw medical image data 52 in a coordinate system of probe 12 on a data memory 22, and, in accordance with instructions received via a user interface, either perform a scan conversion 56 on the raw medical image data and display 64 a resulting medical image 70 at a first resolution on an integrated display 14; or at least one of transfer raw data 68 to an external device 24 for further processing or storage, or perform a scan conversion 56 on the raw medical image data and display 64 a resulting medical image 72 at a second, higher resolution on an external display 24.

Embodiments of the present invention are not limited to ultrasound machines as a hand carried medical imaging device 10. For example, images can be provided from other probes 12, such as a medical endoscope probe.

While the invention has been described in terms of various specific embodiments, those skilled in the art will recognize that the invention can be practiced with modification within the spirit and scope of the claims.

What is claimed is:

1. A portable ultrasound system comprising:
a probe to acquire ultrasound data of an object; and
a handheld or hand carried device comprising:
a built-in integrated display;
a memory to store the ultrasound data as acquired by the probe; and
a processor configured to process the stored ultrasound data to generate (i) a first image at a resolution at or below a maximum resolution of the built-in integrated display and (ii) a second image that is at least three times the resolution of the built-in integrated display in at last one dimension for storage or offline display.

2. The portable ultrasound system of claim 1, wherein the processor is further configured to transfer the second image to an external device.

3. The portable ultrasound system of claim 2, wherein the external device includes a display capable of displaying the second image at the resolution greater than the maximum resolution of the built-in integrated display.

4. The portable ultrasound system of claim 1, wherein the processor is configured to transfer the second image to the external device via one of a wired network or a wireless network.

5. The portable ultrasound system of claim 1, wherein the built-in integrated display comprises a first portion to present the first image and a second portion to present labels corresponding one or more functions performed by a plurality of soft keys.

6. The portable ultrasound system of claim 1, wherein the stored ultrasound data is non-scan-converted ultrasound data and accessible from the memory after generating the first and second images.

7. The portable ultrasound system of claim 1, wherein the maximum resolution of the built-in integrated display is 320 pixels in at least one of a horizontal and vertical direction.

8. The portable ultrasound system of claim 1, wherein the second image is generated for display at a resolution of at least 1028 pixels in at least one of a horizontal and vertical direction.

9. The portable ultrasound system of claim 1, wherein the second image is generated for display at a resolution of at least 640 pixels in at least one of a horizontal and vertical direction.

10. The portable ultrasound system of claim 1, wherein the probe acquires the ultrasound data from a fan-like region of lines.

11. The portable ultrasound system of claim 1, wherein the memory is a software memory and the processor is a general purpose processor, the software memory including instructions to instruct the general purpose processor to control back end processing of the stored ultrasound data.

12. A method for operating a portable ultrasound system having a handheld or hand carried device including a built-in integrated display and a probe, the method comprising:
acquiring ultrasound data of an object using the probe of the portable ultrasound system; storing the ultrasound data as acquired by the probe in the handheld or hand carried device of the portable ultrasound system; and
generating from the stored ultrasound data using the handheld or hand carried device of the portable ultrasound system (i) a first image at a resolution at or below a maximum resolution of the built-in integrated display and (ii) a second image that is at least three times the resolution of the built-in integrated display in at last one dimension for storage or offline display.

13. The method of claim 12, further comprising displaying the first image on the built-in integrated display and transferring the second image to an external device having a display capable of displaying the second image at the resolution greater than the maximum resolution of the built-in integrated display.

14. The method of claim 13, wherein transferring the second image comprises transferring the second image to the external device via one of a wired network or a wireless network.

15. The method of claim 12, wherein generating the first and second images using the portable ultrasound system comprises scan-converting the stored ultrasound data at a first site where the ultrasound data is acquired, and further comprising transferring the second image to an external device at a site remote from the portable ultrasound system.

16. The method of claim 12, wherein generating the first and second images comprises scan converting a same sub-set of the stored ultrasound data.

17. A system for ultrasound imaging, the system comprising:
a portable ultrasound imaging device in combination with an external device, wherein,
the portable ultrasound imaging device having a probe to acquire ultrasound data of an object and a handheld or hand carried device including an integrated display, the handheld or hand carried device further having a memory to store the ultrasound data as non-scan-converted ultrasound data acquired by the probe and a processor configured to (i) process the stored non-scan-converted ultrasound data to generate, as a lower resolution image, an image at a resolution at or below a maximum resolution of the integrated display and (ii) transfer the stored non-scan-converted ultrasound data to the external device; and
the external device is configured to receive the non-scan-converted ultrasound data transferred from the portable ultrasound imaging device and having a processor configured to process the received non-scan-converted ultrasound data to generate, as a higher resolution image, an image at a resolution above the maximum resolution of the integrated display.

18. The system of claim 17, wherein the processor of the portable ultrasound imaging device is configured to process the stored ultrasound data to generate the higher resolution image.

19. The system of claim 17, wherein the external device includes a display capable of displaying the higher resolution image.

20. The system of claim 17, wherein the processor of the portable ultrasound imaging device is configured to transfer the stored ultrasound data to the external device via one of a wired network or a wireless network.

21. The system of claim 17, wherein the integrated display comprises a first portion to present the lower resolution image and a second portion to present labels corresponding one or more functions performed by a plurality of soft keys.

22. The system of claim 17, wherein the stored non-scan-converted ultrasound data is accessible from the memory after generating the lower resolution image.

23. The system of claim 17, wherein the maximum resolution of the integrated display is 320 pixels in at least one of a horizontal and vertical direction and the external device further comprising a display having a resolution of at least 1028 pixels in at least one of a horizontal and vertical direction, the higher resolution image being at least 1028 pixels in at least one of the horizontal and vertical direction.

24. The system of claim 17, wherein the probe acquires the ultrasound data from a fan-like region of lines.

25. The system of claim 17, wherein the memory of the portable ultrasound imaging device is a software memory and the processor of the portable ultrasound imaging device is a general purpose processor, the software memory including instructions to instruct the general purpose processor to control back end processing of the stored ultrasound data.

26. A method for ultrasound imaging, the method comprising:
acquiring ultrasound data using a probe of a portable ultrasound system;

storing the ultrasound data as non-scan-converted ultrasound data acquired by the probe in a handheld or hand carried device of the portable ultrasound system;

generating, as a lower resolution image, from the stored non-scan-converted ultrasound data using the handheld or hand carried device, an image at a resolution at or below a maximum resolution of an integrated display of the portable ultrasound system;

transferring the stored non-scan-converted ultrasound data to an external device; and generating, as a higher resolution image, from the non-scan-converted ultrasound data transferred from the portable ultrasound system using the external device, an image at a resolution above the maximum resolution of the integrated display.

27. The method of claim 26, further comprising displaying the lower resolution image on the integrated display and displaying the higher resolution image on a display of the external device.

28. The method of claim 26, wherein generating the lower resolution image and the higher resolution image comprises scan-converting from a same sub-set of the ultrasound data.

29. The method of claim 26, wherein transferring the stored ultrasound data comprises transferring the stored ultrasound data to the external device via one of a wired network or a wireless network.

30. The method of claim 26, wherein generating the lower resolution image with the portable ultrasound system is performed at a first site where the ultrasound data is acquired, and generating the higher resolution image is performed at a site remote from the portable ultrasound system.

31. The method of claim 26, wherein the stored non-scan-converted ultrasound data is accessible from the memory to generate an image at a different resolution after generating the lower resolution image or the higher resolution image.

* * * * *